US005795616A

United States Patent [19]

Greenberg

[11] Patent Number: 5,795,616
[45] Date of Patent: Aug. 18, 1998

[54] ENHANCED FLAVORS USING 2'-HYDROXYPROPIOPHENONE

[75] Inventor: Michael J. Greenberg, Northbrook, Ill.

[73] Assignee: Wm. Wrigley Jr. Company, Chicago, Ill.

[21] Appl. No.: 577,449

[22] Filed: Dec. 21, 1995

[51] Int. Cl.$^6$ ............................................. A23G 3/30
[52] U.S. Cl. ............................. 426/650; 426/651; 424/49
[58] Field of Search ................... 426/650, 651; 424/49

[56] References Cited

U.S. PATENT DOCUMENTS

| | | | |
|---|---|---|---|
| 3,900,582 | 8/1975 | Winter et al. | 426/535 |
| 3,917,872 | 11/1975 | Winter et al. | 426/537 |
| 3,924,015 | 12/1975 | Winter et al. | 426/538 |
| 3,931,166 | 1/1976 | Winter et al. | 260/250 |
| 3,931,245 | 1/1976 | Winter et al. | 260/347.2 |
| 3,931,246 | 1/1976 | Winter et al. | 260/347.2 |
| 3,947,603 | 3/1976 | Winter et al. | 426/538 |
| 3,952,024 | 4/1976 | Winter et al. | 206/347.2 |
| 3,952,026 | 4/1976 | Winter et al. | 260/347.8 |
| 3,989,713 | 11/1976 | Winter et al. | 260/326.2 |
| 4,085,109 | 4/1978 | Winter et al. | 260/294.8 E |
| 4,126,618 | 11/1978 | Winter et al. | 546/339 |
| 4,138,410 | 2/1979 | Winter et al. | 260/332.2 R |
| 4,303,689 | 12/1981 | Winter et al. | 426/537 |
| 5,128,154 | 7/1992 | Johnson et al. | 426/3 |

OTHER PUBLICATIONS

P. R. Ashurst (ed.), Food Flavorings, 1991 AVI/Van Nostrand Reinhold, p. 209.

*Primary Examiner*—James H. Reamer
*Attorney, Agent, or Firm*—Gordon McGrew

[57] ABSTRACT

2'-Hydroxypropiophenone is used as a flavorant to enhance the flavor of wintergreen-flavored products and to contribute a wintergreen note to non-wintergreen-flavored products. The compound may be used as a partial or complete replacement for methyl salicylate used as a flavorant in products. The invention is intended for use in orally consumed products such as chewing gums, mouthwashes, toothpastes, pharmaceuticals, foods, beverages and candies.

30 Claims, No Drawings

ENHANCED FLAVORS USING 2'-HYDROXYPROPIOPHENONE

BACKGROUND OF THE INVENTION

The present invention relates to the use of 2'-hydroxypropiophenone as a flavor ingredient. More particularly, the present invention relates to the use of 2'-hydroxypropiophenone as an enhancement, or as complete or partial replacement for methyl salicylate in chewing gum, foods, dentrifices, mouthwashes and other orally consumable compositions.

Methyl salicylate is a commonly used flavor and fragrance compound which provides the characteristic flavor of wintergreen to foods, beverages, candies, chewing gums and oral care products. It is also used to enhance the flavor of mint flavored products, for example, those flavored primarily with peppermint or spearmint oils. Methyl salicylate is also used as an active ingredient in topically applied anesthetic ointments promoted for relief of muscle aches, arthritis and similar complaints. Salicylic acid derivatives, most notably acetyl salicylic acid (more commonly known as aspirin), often have pharmaceutical properties such as anagestic, anticoagulant, antipyretic and anti-fungal activity. Not surprisingly, these pharmaceutical agents are generally toxic to some degree. Methyl salicylate itself is known to be toxic at dosage levels well above those found in oral products.

While products flavored with methyl salicylate have gained widespread consumer acceptance, the use of such a compound with pharmaceutical properties and a degree of toxicity poses a potential risk of adverse publicity or governmental regulation which could limit the level at which it may be used, or prohibit it entirely. The availability of a replacement compound for methyl salicylate would be highly desirable.

U.S. Pat. Nos. 4,303,689; 4,138,410; 4,126,618; 4,085,109; 3,989,713; 3,952,026; 3,952,024; 3,947,603; 3,931,246; 3,931,245; 3,931,166; 3,924,015; 3,917,872 and 3,900,582 to Winter disclose several hundred compounds useful as flavoring agents.

P. R. Ashurst (ed. Food Flavourings, p209, AVI, New York, 1991) describes a confectionery flavoring composition called Winter flavor which is composed of peppermint oil and other common natural flavorants.

Until now, it is believed that no satisfactory, non-salicylate substitute for methyl salicylate in flavoring compositions has been proposed.

SUMMARY OF THE INVENTION

The present invention provides improved flavor for products. In the present invention, the term "products" refers to manufactured goods which are intended to be orally consumed or at least taken into the oral cavity. Products include foods, beverages, confections, pharmaceuticals, chewing gums, mouthwashes, toothpastes and other items meeting the above definition. Accordingly, the present invention provides for the use of 2'-hydroxypropiophenone in flavorant compositions used in such products to enhance or replace methyl salicylate. When used as a replacement for methyl salicylate, the compound may be used alone or in combination with other wintergreen-like flavor components and the replacement may be partial or complete.

In accordance with one embodiment of the present invention a wintergreen-flavored product comprising, as a flavorant, methyl salicylate is enhanced by addition of 2'-hydroxypropiophenone. Preferably, the weight ratio of methyl salicylate to 2'-hydroxypropiophenone in the product is between about 1:1 and 10:1, more preferably between about 2:1 and 4:1 and most preferably about 3:1.

In an embodiment, a method of reducing the level of methyl salicylate in a wintergreen-flavored product formulation is provided. The method comprises the steps of modifying a wintergreen-flavored product formulation by substituting 2'-hydroxypropiophenone for at least a portion of the methyl salicylate. Optionally, other flavor components having flavor similar to methyl salicylate are also present. In an embodiment, all of the methyl salicylate is replaced. In an embodiment 10 to 50% by weight of the methyl salicylate is replaced. In an embodiment, about 25% by weight of the methyl salicylate is replaced.

In an embodiment, a salicylate-free, wintergreen-flavored product comprises 2'-hydroxypropiophenone and optionally other non-salicylate flavor components.

In an embodiment, a method of adding a wintergreen flavor note to a non-wintergreen-flavored product comprises the steps of formulating a non-wintergreen flavor, adding 2'-hydroxypropiophenone to the flavor, and adding the flavor to the product. In an embodiment, 2'-hydroxypropiophenone comprises 1 to 35% by weight of the flavor. In an embodiment, 2'-hydroxypropiophenone comprises 5 to 20% by weight of the flavor.

In an embodiment, a chewing gum comprises a gum base, a sweetener and a flavor which comprises 2'-hydroxypropiophenone. In an embodiment, the chewing gum is a wintergreen-flavored chewing gum. In an embodiment, the chewing gum contains from about 0.01 to about 1.0% 2'-hydroxypropiophenone by weight of the chewing gum. In an embodiment, the chewing gum contains from about 0.05 to about 0.40% 2'-hydroxypropiophenone by weight of the chewing gum.

With the forgoing in mind, it is a feature and advantage of the present invention to enhance the flavor of wintergreen-flavored products.

It is also a feature and advantage of the present invention to reduce or eliminate the need for methyl salicylate in wintergreen-flavored products.

It is also a feature and advantage of the present invention to provide a wintergreen flavor note to orally consumed products without the use of methyl salicylate.

It is also a feature and advantage of the present invention to provide an improved oral product.

It is also a feature and advantage of the present invention to provide an improved wintergreen-flavored chewing gum.

Additional features and advantages of the present invention are described in, and will be apparent from, the detailed description of the presently preferred embodiments.

DETAILED DESCRIPTION AND PREFERRED EMBODIMENTS OF THE INVENTION

Methyl Salicylate (2-hydroxybenzoic acid methyl ester) is a commonly used flavorant. It was originally derived from natural sources but now is primarily produced by esterification of salicylic acid with methanol. Methyl Salicylate has the following structure:

Methyl Salicylate

Not surprisingly, other salicylates, that is esters of salicylic acid, may have flavor similar to methyl salicylate. In particular, ethyl salicylate has such a flavor.

The inventor has now made the surprising discovery of a non-salicylate compound which has a flavor similar to methyl salicylate and which can enhance the flavor of methyl salicylate. This allows the compound to be substituted for methyl salicylate at levels of 5 to 100% by weight of the original quantity of methyl salicylate, depending on the application. The compound may be used in wintergreen flavored compositions as well as in compositions flavored with mint oils and other compatible flavor systems. The compound is 2'-hydroxypropiophenone and has the following structure:

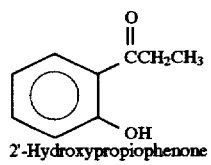

2'-Hydroxypropiophenone

It is available from Aldrich, 1001 West Saint Paul Avenue, Milwaukee, Wis. 53233 USA. A synthesis for the compound may be found in Org. Synth. 13, 90 (1933).

The present invention contemplates the use of 2'-hydroxypropiophenone as a flavorant for chewing gums, candies, dentrifices, mouth washes and other food and oral compositions. In products where methyl salicylate is presently used, 2'-hydroxypropiophenone may be used to enhance the wintergreen flavor or to replace a portion or all of that compound.

In new formulations, 2'-hydroxypropiophenone may be used as the sole flavorant or it may be combined with other flavor compounds to impart a wintergreen flavor or wintergreen note to the composition. More particularly, 2'-hydroxypropiophenone may be blended with peppermint oil, spearmint oil, menthol, cinnamon flavor, anise, root beer flavor, bubble gum flavor, spice flavors, citrus oils and fruit flavors. Such flavor compositions may include natural or artificial components or blends of the two. Combinations of 2'-hydroxypropiophenone with cooling agents such as menthol, menthone ketals, N-substituted-p-menthane carboxamides and 3-1-menthoxypropane-1,2-diol are specifically completed. 2'-hydroxypropiophenone may comprise from about 1 to about 99 weight percent of the complete flavor blend. Preferably, the blend comprises 20 to 80% 2'-hydroxypropiophenone. The precise usage level will depend on the nature of the desired flavor of the final product and the preferences of the flavorist compounding the flavor composition.

In a preferred embodiment, the flavored product is a chewing gum. Chewing gums typically contain about 0.25 to about 5%, and most typically about 1% flavor by weight.

In general, a chewing gum comprises a water-soluble bulk portion, a water-insoluble chewable gum base portion and typically, water-insoluble flavor ingredients. The water-soluble bulk portion dissipates with a portion of the flavor over time during chewing. The gum base portion is retained in the mouth throughout the chew.

The insoluble gum base generally comprises elastomers, resins, fats and oils, waxes, softeners and inorganic fillers. The insoluble gum base constitutes between about 5% to about 95% of the gum, and more preferably about 20% to 30%. All percent values represent weight percent.

The gum base typically also includes a filler component. The filler component may be calcium carbonate, magnesium carbonate, talc, dicalcium phosphate, and the like. The filler may constitute between about 5% to about 60% of the gum base. Preferably, the filler comprises about 5% to about 50% of the gum base. The gum base also contains softeners, including glycerol monostearate and glycerol triacetate. Further, gum bases may also contain additional ingredients such as antioxidants, colors, and emulsifiers. The present invention contemplates using any commercially acceptable gum base.

The water-soluble portion of chewing gum may further comprise softeners, sweeteners, and flavors and combinations thereof. The softeners are added to the chewing gum to optimize the chewing ability and mouth feel of the gum. Softeners, also known in the art as plasticizers, generally constitute about 0.1% to about 15% of the chewing gum. Softeners contemplated by the present invention include glycerin, lecithin and combinations thereof. Aqueous sweetener solutions such as those containing sorbitol, hydrogenated starch hydrolysates, corn syrup, and combinations thereof may be used as softeners and binding agents in gum.

Sweeteners contemplated by the present invention for use in chewing gum include both sugar and sugarless components. Sugar sweeteners generally include saccharide-containing components commonly known in the art and include, but are not limited to, sucrose, dextrose, maltose, dextrin, dried invert sugar, fructose, levulose, galactose, corn syrup solids and the like, alone or in any combination. Sugarless sweeteners include components with sweetening characteristics but are devoid of the commonly known sugars and comprise, but are not limited to, sugar alcohols such as sorbitol, mannitol, xylitol, hydrogenated starch hydrolysates, maltitol, hydrogenated isomaltulose and the like, alone or in any combination. Also contemplated for direct addition to the gum are high intensity sweeteners such as aspartame, sucralose, cyclamate, acesulfame-K, dihydrochalones, glycyrrhizin, alitame, and saccharin, and the food acceptable salts thereof.

Those persons skilled in the art will recognize that any combination of sugar/sugarless sweeteners may be employed in the chewing gum. Further, those skilled in the art will recognize a sweetener may be present in a chewing gum in whole or in part as a water-soluble bulking agent, and that the softener may be combined with a sweetener such as an aqueous sweetener solution.

In general, chewing gum is manufactured by sequentially adding the various chewing gum ingredients to any commercially available mixer known in the art. After the ingredients have been thoroughly mixed, the gum mass is discharged from the mixer and shaped into the desired forms such as by rolling into sheets and cutting into sticks, extruding into chunks, or casting into pellets. Generally, the ingredients are mixed by first melting gum base and adding it to the running mixer. The base may also be melted in the mixer itself. Color may also be added at this time. A softener such as glycerin may then be added next along with the syrup and a portion of bulking agent. Further portions of the bulking agents may be added to the mixer.

Preferably, the flavor ingredients are added to the gum mixture near the end of the mixing process. The entire mixing procedure takes from about 5 minutes to 15 minutes, however, longer mixing times may be required. Those persons skilled in the art will recognize that many variations of the above described procedure may be followed.

In other embodiments, the flavored product is a food, candy, mouthwash, toothpaste, or other oral product.

EXAMPLES

By way of example and not limitation the following examples will now be given.

Examples 1–4 demonstrate replacement of methyl salicylate with 2'-hydroxypropiophenone in a sweet water taste test.

Example 1

A control solution for taste testing was prepared by dissolving 0.2 ml of methyl salicylate in 10 ml of ethanol. One milliliter of this solution was dissolved in 100 ml of a 5% sucrose aqueous solution.

Example 2

A solution was prepared as in Example 1 except that 0.02 ml of methyl salicylate was replaced with 2'-hydroxypropiophenone (10% replacement).

Example 3

A solution was prepared as in Example 1 except that 0.05 ml of methyl salicylate was replaced with 2'-hydroxypropiophenone (25% replacement).

Example 4

A solution was prepared as in Example 1 except that 0.10 ml of methyl salicylate was replaced with 2'-hydroxypropiophenone (50% replacement).

The samples were evaluated for order and taste by five experienced judges with the following results:

| | Replacement Level | Evaluation/Comments |
|---|---|---|
| Example 1 | 0% | Okay |
| Example 2 | 10% | Okay/good to very good |
| Example 3 | 25% | Slightly astringent, slightly sweeter, slightly floral |
| Example 4 | 50% | Astringent mouth feel, slightly bitter, sweet, slightly burning, slightly perfumery, medicinal, slight anise note. |

Examples 5 through 8 illustrate, by way of example, the practice of various embodiments of the present invention.

Example 5

A wintergreen flavored toothpaste having enhanced wintergreen flavor is prepared from the following formula:

| | Percent By Weight |
|---|---|
| Xylitol | 10.00 |
| Carboxymethylcellulose | 0.90 |
| Glycerin | 9.99 |
| Sorbitol | 7.00 |
| Sodium benzoate | 0.50 |
| Water | 19.60 |
| Sodium monofluorophosphate | 0.76 |

| | Percent By Weight |
|---|---|
| Titanium dioxide | 0.40 |
| Insoluble sodium metaphosphate | 41.85 |
| Hydrated Alumina | 1.00 |
| Sodium lauryl sulfate | 2.00 |
| Anhydrous dicalcium phosphate | 5.00 |
| Flavor: | |
| Peppermint Oil | 0.15 |
| Methyl Salicylate | 0.68 |
| 2'-hydroxypropiophenone | 0.17 |
| | 100.00 |

Example 6

A wintergreen-flavored chewing gum having a reduced methyl salicylate level is prepared according to the following formula:

| | Percent By Weight |
|---|---|
| Sugar | 62.44 |
| Base | 22.00 |
| Corn Syrup | 12.50 |
| Glycerin | 1.40 |
| Color | 0.04 |
| Lecithin | 0.12 |
| Flavor: | |
| Peppermint Oil | 0.40 |
| Menthol | 0.15 |
| Methyl Salicylate | 0.72 |
| 2'-hydroxypropiophenone | 0.23 |
| | 100.00 |

In this case, 0.95% methyl salicylate is replaced by 0.72% methyl salicylate and 0.23% 2'-hydroxypropiophenone to reduce the methyl salicylate by 24%.

Example 7

The chewing gum of Example 6 is formulated to be salicylate-free by substituting the following flavor compounds for those in Example 6:

| | Percent By Weight |
|---|---|
| Flavor: | |
| Peppermint Oil | 0.55 |
| Menthol | 0.15 |
| 2'-hydroxypropiophenone | 0.45 |
| 2-ethyl-benzofuran | 0.20 |
| 5,5'-dimethyl-2,2'-difuryl-methane | 0.10 |
| difurfuryl ether | 0.05 |

Example 8

A peppermint flavored mouthwash is given a wintergreen note without addition of methyl salicylate according to the following formula:

|  | Percent By Weight |
| --- | --- |
| Ethyl alcohol (95%) | 5.00 |
| Glycerin | 2.00 |
| Zinc Oxide | 0.10 |
| Citric Acid | 0.50 |
| Sodium Fluoride | 0.05 |
| Sodium Laural Sulfate | 1.00 |
| Saccharin Acid | 0.06 |
| Sodium Hydroxide | 0.15 |
| Color | 1.00 |
| Flavor: | |
| Peppermint Oil | 0.12 |
| Spearmint Oil | 0.01 |
| 2'-hydroxypropiophenone | 0.01 |
| Water | 90.00 |
|  | 100.00 |

Although specific embodiments and examples have been described herein, it should be born in mind that these have been provided by way of explanation and illustration and that the present invention is not limited thereby. Modifications that are within the ordinary skill in the art to make are considered to lie within the scope of the invention as defined by the following claims, including all equivalents.

I claim:

1. A wintergreen-flavored product comprising as a flavorant, methyl salicylate and about 1 to about 99 weight percent 2'-hydroxypropiophenone.

2. The wintergreen-flavored product of claim 1 wherein the weight ratio of methyl salicylate to 2'-hydroxypropiophenone is from about 1:1 to 10:1.

3. The wintergreen-flavored product of claim 1 wherein the weight ratio of methyl salicylate to 2'-hydroxypropiophenone is from about 2:1 to 4:1.

4. The wintergreen-flavored product of claim 1 wherein the weight ratio of methyl salicylate to 2'-hydroxypropiophenone is about 3:1.

5. The wintergreen-flavored product of claim 1 wherein the product is a chewing gum.

6. The wintergreen-flavored product of claim 1 wherein the product is a toothpaste.

7. The wintergreen-flavored product of claim 1 wherein the product is a mouthwash.

8. The wintergreen-flavored product of claim 1 wherein the product is a candy.

9. A method of reducing the level of methyl salicylate in a wintergreen-flavored product formulation comprising the step of substituting in the formulation 2'-hydroxypropiophenone for 5 to 100 percent by weight of the methyl salicylate.

10. The method of claim 9 wherein all of the methyl salicylate is replaced.

11. The method of claim 9 wherein 10 to 50% by weight of the methyl salicylate is replaced.

12. The method of claim 9 wherein the product formulation is a chewing gum formulation.

13. A product comprising as a wintergreen flavorant, 2'-hydroxypropiophenone.

14. The product of claim 13 wherein the product also comprises other non-salicylate flavorants.

15. The product of claim 13 wherein the product is a chewing gum.

16. The product of claim 13 wherein the product is a toothpaste.

17. The product of claim 13 wherein the product is a mouthwash.

18. The product of claim 13 wherein the product is a beverage.

19. The product of claim 13 wherein the product is a candy.

20. A method of adding a wintergreen flavor note to a non-wintergreen-flavored product comprising the steps of:

formulating a non-wintergreen flavor, adding 1 to 99 percent 2'-hydroxypropiophenone by weight of the complete flavor to the flavor, and adding the flavor to the product.

21. The method of claim 20 wherein the flavor comprises 1 to 35% by weight 2'-hydroxypropiophenone.

22. The method of claim 20 wherein the flavor comprises 5 to 20% by weight 2'-hydroxypropiophenone.

23. The method of claim 20 wherein the product is a chewing gum.

24. The method of claim 20 wherein the product is a beverage.

25. A chewing gum comprising a gum base, a sweetener and 2'-hydroxypropiophenone.

26. The chewing gum of claim 25 comprising from about 0.01% to about 1.0% by weight 2'-hydroxypropiophenone.

27. The chewing gum of claim 25 comprising from about 0.05% to about 0.40% by weight 2'-hydroxypropiophenone.

28. The chewing gum of claim 25 wherein the chewing gum is a wintergreen-flavored chewing gum.

29. The chewing gum of claim 25 wherein the chewing gum also includes methyl salicylate.

30. A salicylate free, wintergreen-flavored chewing gum comprising as a flavorant, from about 0.01 percent to about 1.0 percent 2'-hydroxypropiophenone by weight of the chewing gum.

* * * * *